United States Patent
Nomaru

(10) Patent No.: US 9,470,516 B2
(45) Date of Patent: Oct. 18, 2016

(54) UNEVENNESS DETECTING DEVICE

(71) Applicant: DISCO CORPORATION, Tokyo (JP)

(72) Inventor: Keiji Nomaru, Tokyo (JP)

(73) Assignee: Disco Corporation, Tokyo (JP)

( * ) Notice: Subject to any disclaimer, the term of this patent is extended or adjusted under 35 U.S.C. 154(b) by 35 days.

(21) Appl. No.: 14/667,994

(22) Filed: Mar. 25, 2015

(65) Prior Publication Data

US 2015/0287179 A1   Oct. 8, 2015

(30) Foreign Application Priority Data

Apr. 7, 2014   (JP) .................................. 2014-078504

(51) Int. Cl.
| | | |
|---|---|---|
| *G06K 9/62* | (2006.01) | |
| *G01B 11/30* | (2006.01) | |
| *G01N 21/95* | (2006.01) | |

(52) U.S. Cl.
CPC ......... *G01B 11/306* (2013.01); *G01N 21/9501* (2013.01)

(58) Field of Classification Search
None
See application file for complete search history.

(56) References Cited

U.S. PATENT DOCUMENTS 9,140,546 B2 *   9/2015   Maison ................... G01B 11/25
2008/0170243 A1 *   7/2008   Nomaru ................. B23K 26/03
356/634

FOREIGN PATENT DOCUMENTS

| JP | 05-326700 | 12/1993 |
|---|---|---|
| JP | 07-045556 | 2/1995 |
| JP | 2002-319559 | 10/2002 |
| JP | 2008-012566 | 1/2008 |

\* cited by examiner

*Primary Examiner* — Brian P Werner
(74) *Attorney, Agent, or Firm* — Greer Burns & Crain, Ltd.

(57) ABSTRACT

An unevenness detecting device includes: a pulsed illuminating light source emitting light having a predetermined wavelength range; a first condensing lens condensing return light reflected by a workpiece held on a chuck table and passed through a chromatic aberration lens and a half-silvered mirror; a mask disposed at the position of a focal point of the first condensing lens, the mask passing only the condensed return light; a diffraction grating performing light separation so as to correspond to the wavelengths of the return light; a second condensing lens condensing the return light resulting from the light separation by the diffraction grating; and an imaging element disposed at the position of a focal point of the second condensing lens.

3 Claims, 9 Drawing Sheets

UNEVENNESS DETECTING DEVICE

BACKGROUND OF THE INVENTION

1. Field of the Invention

The present invention relates to an unevenness detecting device detecting the processed state of a processed groove such as a laser-processed groove, a cut groove, or the like processed in a workpiece such as a wafer or the like or the state of unevenness of traces of grinding on a ground workpiece surface.

2. Description of the Related Art

In a semiconductor device manufacturing process, a plurality of regions are partitioned by scheduled division lines arranged in a lattice manner on the top surface of a wafer having substantially the shape of a disk, and devices such as ICs, LSIs, or the like are formed in the partitioned regions. Then, after the undersurface of the wafer is ground to form the wafer with a predetermined thickness, the regions in which the devices are formed are divided from each other by cutting the wafer along the scheduled division lines. The individual devices are thus manufactured.

A grinding device for grinding the undersurface of a wafer includes a chuck table holding the wafer, grinding means including a grinding wheel grinding the wafer held on the chuck table, thickness measuring means for measuring the thickness of the wafer, and the like (see for example Japanese Patent Laid-Open No. 2002-319559).

In addition, the above-described division along the scheduled division lines of the wafer is performed by a cutting device or a laser processing device. The cutting device includes a chuck table holding a wafer, cutting means including a cutting blade cutting the wafer held on the chuck table, imaging means for detecting scheduled division lines formed on the wafer held on the chuck table, and the like (see for example Japanese Patent Laid-Open No. Hei 7-45556).

In addition, the laser processing device includes a chuck table holding a wafer, laser beam irradiating means for irradiating the wafer held on the chuck table with a laser beam, imaging means for detecting scheduled division lines formed on the wafer held on the chuck table, and the like (see for example Japanese Patent Laid-Open No. 2008-12566).

The cutting device or the laser processing device detects the state of a cut groove or the state of a laser-processed groove by imaging the cut groove or the laser-processed groove by the imaging means so that processing conditions can be adjusted (see for example Japanese Patent Laid-Open No. Hei 5-326700).

SUMMARY OF THE INVENTION

However, the image imaged by the imaging means is a two-dimensional image of the top surface. Thus, a two-dimensional image at a predetermined depth from the top surface, a three-dimensional image of the depth and sectional shape of the cut groove or the laser-processed groove, or a three-dimensional image of the state of debris or the like cannot be detected, so that the processed state cannot be verified minutely. In addition, the state of unevenness of traces of grinding cannot be verified in the case of the grinding device.

It is accordingly an object of the present invention to provide an unevenness detecting device that makes it possible to accurately verify the processed state of a processed workpiece.

In accordance with an aspect of the present invention, there is provided an unevenness detecting device detecting unevenness of a workpiece retained by workpiece holding means, the unevenness detecting device including: a pulsed illuminating light source emitting light having a predetermined wavelength range; a first converging lens converging the light emitted by the pulsed illuminating light source; a half-silvered mirror branching the light converged by the first converging lens; a chromatic aberration lens condensing the light branched by the half-silvered mirror and irradiating the workpiece retained by the workpiece holding means with the condensed light; a first condensing lens condensing return light reflected by the workpiece retained by the workpiece holding means and passed through the chromatic aberration lens and the half-silvered mirror; a mask disposed at a position of a focal point of the first condensing lens, the mask passing only the condensed return light; a second converging lens converging the return light passed through the mask; a diffraction grating performing light separation so as to correspond to wavelengths of the return light converged by the second converging lens; a second condensing lens condensing the return light resulting from the light separation by the diffraction grating; an imaging element disposed at a position of a focal point of the second condensing lens; control means including a memory storing an image generated by the imaging element; and output means displaying the image stored in the memory of the control means; wherein when a width direction of a detection region in which to detect the unevenness of the workpiece retained by the workpiece holding means is a Y-axis direction, and a longitudinal direction of the detection region is an X-axis direction, the mask has a slit extending in the Y-axis direction, and the imaging element generates a two-dimensional sectional shape in the Y-axis direction on a basis of the return light passed through the slit formed in the mask.

Preferably, the control means stores two-dimensional sectional shapes in the Y-axis direction in the memory while moving the workpiece holding means in the X-axis direction, and generates a three-dimensional shape by arranging, in the X-axis direction, the two-dimensional sectional shapes in the Y-axis direction, the two-dimensional sectional shapes in the Y-axis direction being stored in the memory.

Preferably, the unevenness detecting device is provided to a processing machine including processing means processing the workpiece retained by the workpiece holding means and processing feed means performing processing feed of the workpiece holding means and the processing means relative to each other in the X-axis direction.

In the unevenness detecting device according to the present invention, the mask has the slit extending in the Y-axis direction, and the imaging element generates the two-dimensional sectional shape in the Y-axis direction on the basis of the return light passed through the slit formed in the mask. Thus, the state of unevenness of a laser-processed groove, a cut groove, or the like can be detected in the two-dimensional sectional shape, so that appropriate processing conditions can be set by adjusting laser processing conditions, cutting conditions, or the like.

In addition, two-dimensional sectional shapes in the Y-axis direction are stored in the memory while the workpiece holding means is moved in the X-axis direction, and a three-dimensional shape can be generated by arranging, in the X-axis direction, the two-dimensional sectional shapes in the Y-axis direction which two-dimensional sectional shapes are stored in the memory. Thus, processing conditions such as laser processing conditions, cutting conditions, or the like can be adjusted more precisely on the basis of the three-dimensional shape of the laser-processed groove, the cut groove, or the like.

The above and other objects, features and advantages of the present invention and the manner of realizing them will become more apparent, and the invention itself will best be understood from a study of the following description and appended claims with reference to the attached drawings showing some preferred embodiments of the invention.

DETAILED DESCRIPTION OF THE PREFERRED EMBODIMENTS

Figure 1:
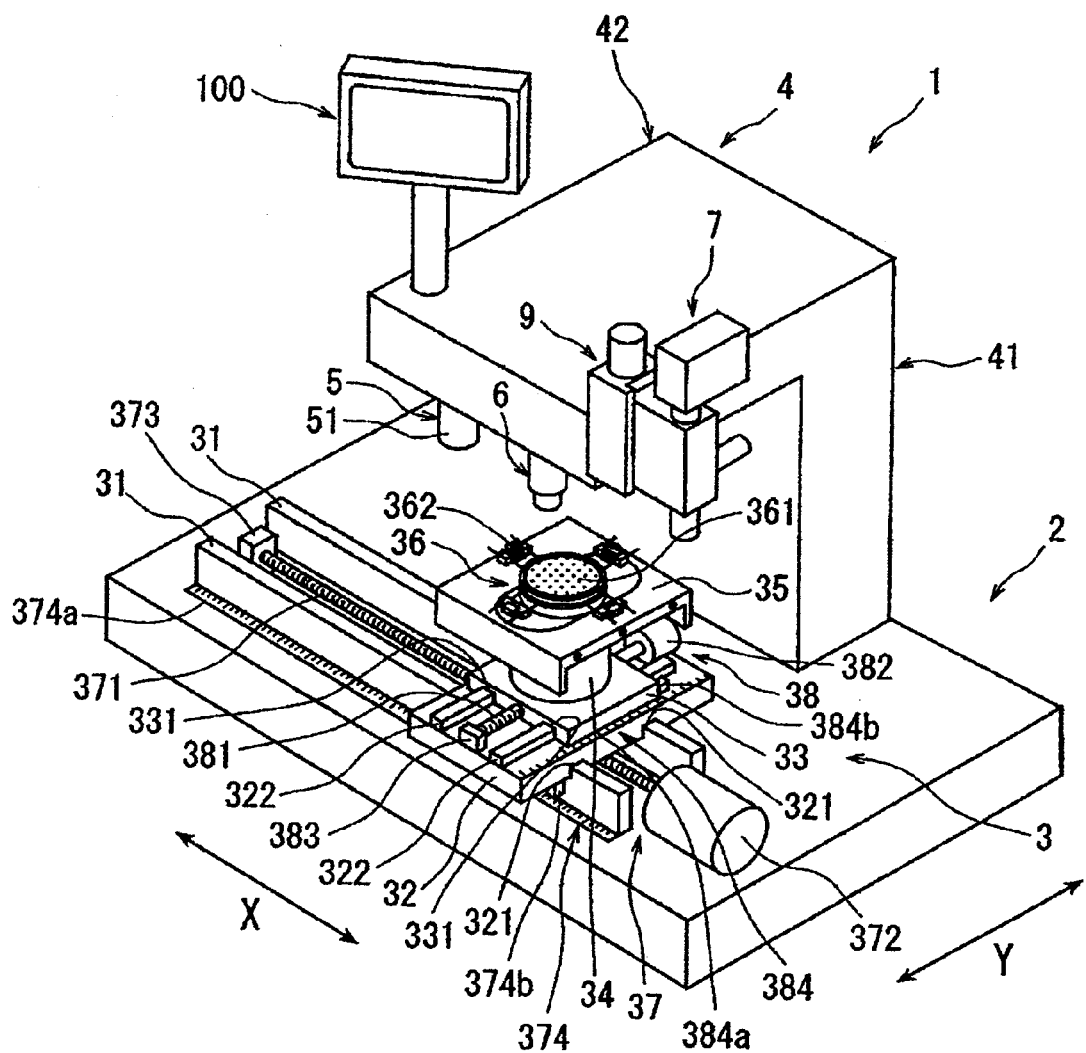
FIG. 1 is a perspective view of a laser processing machine equipped with an unevenness detecting device.

Preferred embodiments of an unevenness detecting device will hereinafter be described in further detail with reference to the accompanying drawings. FIG. 1 is a perspective view of a laser processing machine as a processing machine equipped with the unevenness detecting device. A laser processing machine 1 shown in FIG. 1 includes a stationary base 2, a workpiece holding mechanism 3 holding a workpiece, the workpiece holding mechanism 3 being disposed on the stationary base 2 so as to be movable in a processing feed direction (X-axis direction) indicated by an arrow X, and a laser beam irradiation unit 4 as laser beam irradiating means, which is processing means disposed on the stationary base 2.

The workpiece holding mechanism 3 includes: a pair of guide rails 31 arranged on the stationary base 2 so as to be parallel with each other along the X-axis direction indicated by the arrow X; a first sliding block 32 disposed on the guide rails 31 so as to be movable in the X-axis direction; a second sliding block 33 disposed on the first sliding block 32 so as to be movable in a Y-axis direction orthogonal to the X-axis direction; a cover table 35 supported over the second sliding block 33 by a cylindrical member 34; and a chuck table 36 as workpiece holding means. The chuck table 36 has a suction chuck 361 formed of a porous material. Suction means not shown in the figures holds a semiconductor wafer in a disk shape, for example, as a workpiece onto a holding surface as the upper surface of the suction chuck 361. The thus formed chuck table 36 is rotated by a pulse motor not shown in the figures which pulse motor is disposed within the cylindrical member 34. Incidentally, the chuck table 36 is provided with a clamp 362 for fixing an annular frame that supports the workpiece such as the semiconductor wafer or the like via a protective tape.

The first sliding block 32 is provided with a pair of guided grooves 321 in the undersurface thereof, the pair of guided grooves 321 being fitted to the pair of guide rails 31, and is provided with a pair of guide rails 322 on the top surface thereof, the pair of guide rails 322 being formed in parallel with each other along the Y-axis direction. The thus formed first sliding block 32 is formed so as to be movable in the X-axis direction along the pair of guide rails 31 by fitting the guided grooves 321 to the pair of guide rails 31. The workpiece holding mechanism 3 in the embodiment shown in FIG. 1 has X-axis moving means 37 for moving the first sliding block 32 in the X-axis direction along the pair of guide rails 31. The X-axis moving means 37 includes a male screw rod 371 disposed between and in parallel with the pair of guide rails 31 and a driving source such as a pulse motor 372 or the like for rotation-driving the male screw rod 371. One end of the male screw rod 371 is rotatably supported by a bearing block 373 fixed to the stationary base 2. Another end of the male screw rod 371 is transmissively coupled to an output shaft of the pulse motor 372. Incidentally, the male screw rod 371 is screwed into a through female screw hole formed in a female screw block not shown in the figure which female screw block is provided in a projecting manner on the undersurface of a central portion of the first sliding block 32. Hence, the first sliding block 32 is moved in the X-axis direction along the guide rails 31 by driving the male screw rod 371 for normal rotation and reverse rotation by the pulse motor 372.

The laser processing machine 1 in the present embodiment has X-axis direction position detecting means 374 for detecting the X-axis direction position of the chuck table 36. The X-axis direction position detecting means 374 includes a linear scale 374a disposed along the guide rails 31 and a read head 374b provided to the first sliding block 32 and moving along the linear scale 374a together with the first sliding block 32. The read head 374b of the X-axis direction position detecting means 374 sends a pulse signal of one pulse per μm in the present embodiment to control means to be described later. The control means to be described later detects the X-axis direction position of the chuck table 36 by counting the input pulse signal. Incidentally, when the pulse motor 372 is used as the driving source of the X-axis moving means 37, the X-axis direction position of the chuck table 36 can also be detected by counting driving pulses of the control means to be described later which control means outputs a driving signal to the pulse motor 372. In addition, when a servomotor is used as the driving source of the X-axis moving means 37, the X-axis direction position of the chuck table 36 can also be detected by sending a pulse signal output by a rotary encoder detecting the rotational speed of the servomotor to the control means to be described later, and counting the input pulse signal by the control means.

The second sliding block 33 is provided with a pair of guided grooves 331 in an undersurface thereof, the pair of guided grooves 331 being fitted to the pair of guide rails 322 provided on the top surface of the first sliding block 32. The second sliding block 33 is formed so as to be movable in the Y-axis direction indicated by an arrow Y orthogonal to the X-axis direction by fitting the guided grooves 331 to the pair of guide rails 322. The workpiece holding mechanism 3 in the present embodiment includes Y-axis moving means 38 for moving the second sliding block 33 in the Y-axis direction along the pair of guide rails 322 provided on the first sliding block 32. The Y-axis moving means 38 includes a male screw rod 381 disposed between and in parallel with the pair of guide rails 322 and a driving source such as a pulse motor 382 or the like for rotation-driving the male screw rod 381. One end of the male screw rod 381 is rotatably supported by a bearing block 383 fixed to the top surface of the first sliding block 32. Another end of the male screw rod 381 is transmissively coupled to an output shaft of the pulse motor 382. Incidentally, the male screw rod 381 is screwed into a through female screw hole formed in a female screw block not shown in the figures which female screw block is provided in a projecting manner on the undersurface of a central portion of the second sliding block 33. Hence, the second sliding block 33 is moved in the Y-axis direction along the guide rails 322 by driving the male screw rod 381 for normal rotation and reverse rotation by the pulse motor 382.

The laser processing machine 1 in the present embodiment has Y-axis direction position detecting means 384 for detecting the Y-axis direction position of the second sliding block 33. The Y-axis direction position detecting means 384 includes a linear scale 384a disposed along the guide rails 322 and a read head 384b provided to the second sliding block 33 and moving along the linear scale 384a together with the second sliding block 33. The read head 384b of the Y-axis direction position detecting means 384 sends a pulse signal of one pulse per μm in the embodiment shown in the figures to the control means to be described later. The control means to be described later detects the Y-axis direction position of the chuck table 36 by counting the input pulse signal. Incidentally, when the pulse motor 382 is used as the driving source of the Y-axis moving means 38, the Y-axis direction position of the chuck table 36 can also be detected by counting driving pulses of the control means to be described later which control means outputs a driving signal to the pulse motor 382. In addition, when a servomotor is used as the driving source of the Y-axis moving means 38, the Y-axis direction position of the chuck table 36 can also be detected by sending a pulse signal output by a rotary encoder detecting the rotational speed of the servomotor to the control means to be described later, and counting the input pulse signal by the control means.

The laser beam irradiation unit 4 includes: a supporting member 41 disposed on the stationary base 2; a machine body casing 42 supported by the supporting member 41 and extending substantially horizontally; laser beam irradiating means 5 provided to the machine body casing 42; and imaging means 6 for detecting a processing region to be laser-processed. The laser beam irradiating means 5 includes: pulsed laser beam oscillating means including a pulsed laser beam oscillator and repetition frequency setting means arranged within the machine body casing 42 and not shown in the figures; and a processing head 51 that condenses a pulsed laser beam oscillated by the pulsed laser beam oscillating means and irradiates the workpiece held on the chuck table 36 with the pulsed laser beam.

The imaging means 6 is disposed on the machine body casing 42 at a predetermined distance from the processing head 51 on a same line in the X-axis direction. In addition to an ordinary imaging element (CCD) that performs imaging by visible rays, the imaging means 6 includes infrared illuminating means for irradiating the workpiece with infrared rays, an optical system capturing the infrared rays applied by the infrared illuminating means, an imaging element (infrared CCD) outputting an electric signal corresponding to the infrared rays captured by the optical system, and the like. The imaging means 6 sends the imaged image signal to the control means to be described later.

Figure 2:
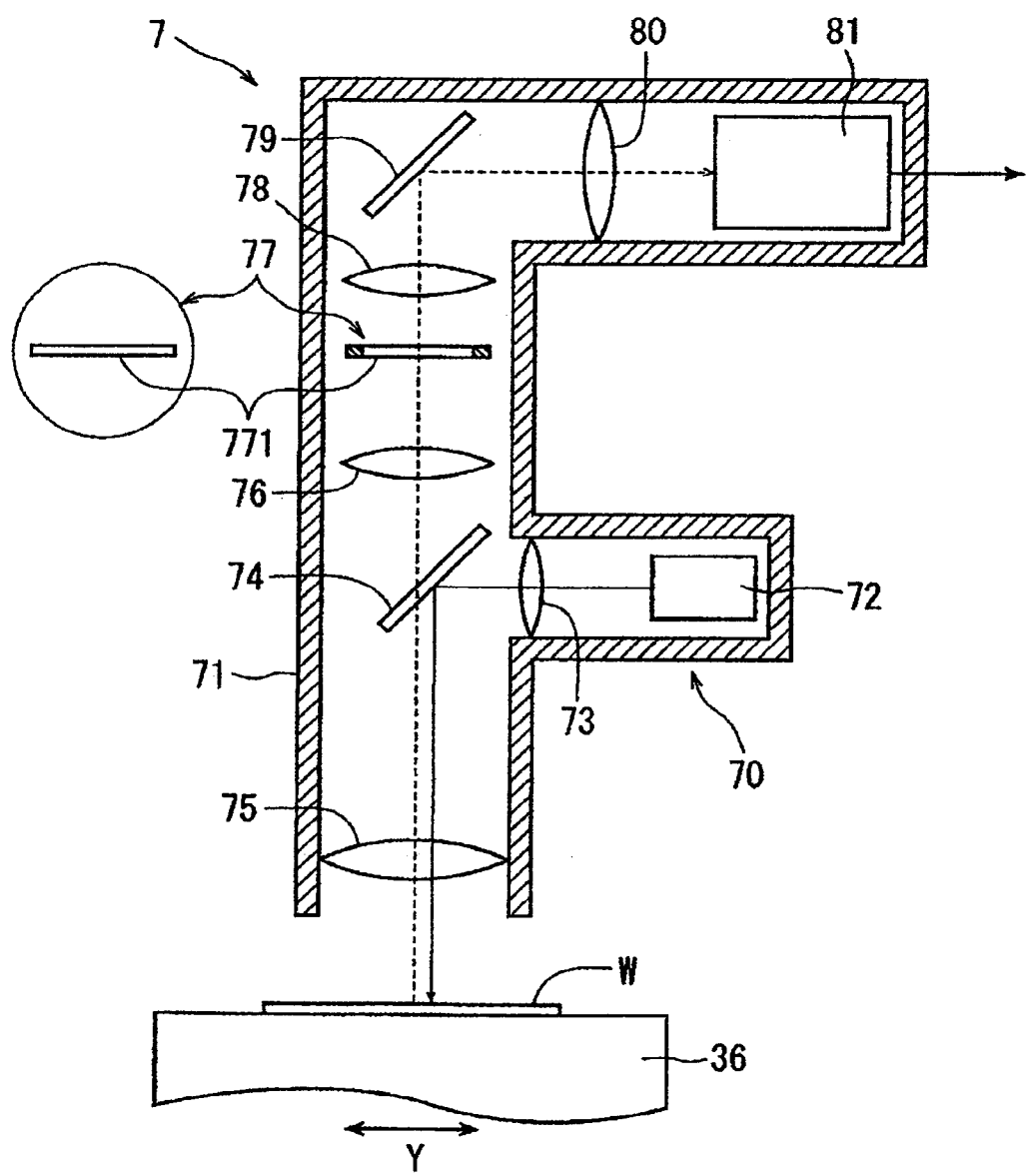
FIG. 2 is a fragmentary sectional view of the unevenness detecting device.
Figure 3:
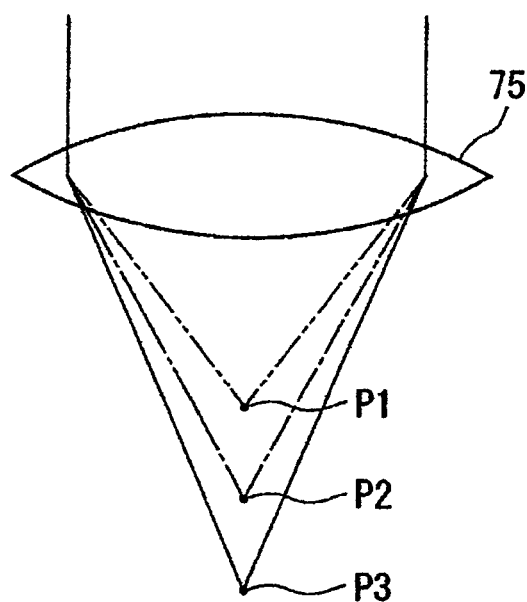
FIG. 3 is a diagram of assistance in explaining the condensing state of a chromatic aberration lens forming the unevenness detecting device shown in FIG. 2.

The laser processing machine 1 in the present embodiment is provided with an unevenness detecting device 7 for detecting a processed state of the processed workpiece held on the chuck table 36. The unevenness detecting device 7 is supported so as to be movable in a Z-axis direction by Z-axis moving means 9 disposed on the machine body casing 42. As shown in FIG. 2, the unevenness detecting device 7 has detection light irradiating means 70 including: a pulsed illuminating light source 72 with a frequency of 10 kHz, for example, the pulsed illuminating light source 72 being disposed in a device housing 71 supported by the Z-axis moving means 9 and having a predetermined wavelength range (for example 400 nm to 800 nm); a first converging lens 73 converging light emitted by the pulsed illuminating light source 72; a half-silvered mirror 74 branching the light converged by the first converging lens 73; and a chromatic aberration lens 75 condensing the light branched by the half-silvered mirror 74 and irradiating a workpiece W held on the chuck table 36 with the condensed light. Incidentally, a xenon flash lamp, a pulsed illuminating white LED, and the like can be used as the above-described pulsed illuminating light source 72. The chromatic aberration lens 75 functions so as to form focal points at positions different according to the wavelengths of light that enters the chromatic aberration lens 75 as shown in FIG. 3. For example, light having a wavelength of 400 nm is condensed at P1, light having a wavelength of 600 nm is condensed at P2, and light having a wavelength of 800 nm is condensed at P3. Incidentally, a distance from the focal point P1 to the focal point P3 is set at 100 μm, for example.

Returning to FIG. 2 and continuing the description, the unevenness detecting device 7 in the present embodiment includes: a first condensing lens 76 condensing return light passed through the chromatic aberration lens 75 and the half-silvered mirror 74, the return light resulting from the workpiece W held on the chuck table 36 reflecting detection light that is applied through the first converging lens 73 forming the detection light irradiating means 70, reflected by the half-silvered mirror 74, and thereby guided to the chromatic aberration lens 75; a mask 77 disposed at the position of a focal point of the first condensing lens 76 to pass only the condensed return light; a second converging lens 78 converging the return light passed through the mask 77; a diffraction grating 79 performing light separation so as to correspond to the wavelengths of the return light converged by the second converging lens 78; a second condensing lens 80 condensing the return light separated by the diffraction grating 79; and an imaging element 81 disposed at the position of a focal point of the second condensing lens 80. Incidentally, a slit 771 extending in the Y-axis direction is formed in the mask 77. The slit 771 in the embodiment shown in the figures has a width (in the X-axis direction orthogonal to the Y-axis direction) set at 0.5 mm, and has a length (in the Y-axis direction) set at 10 mm.

Figure 4:
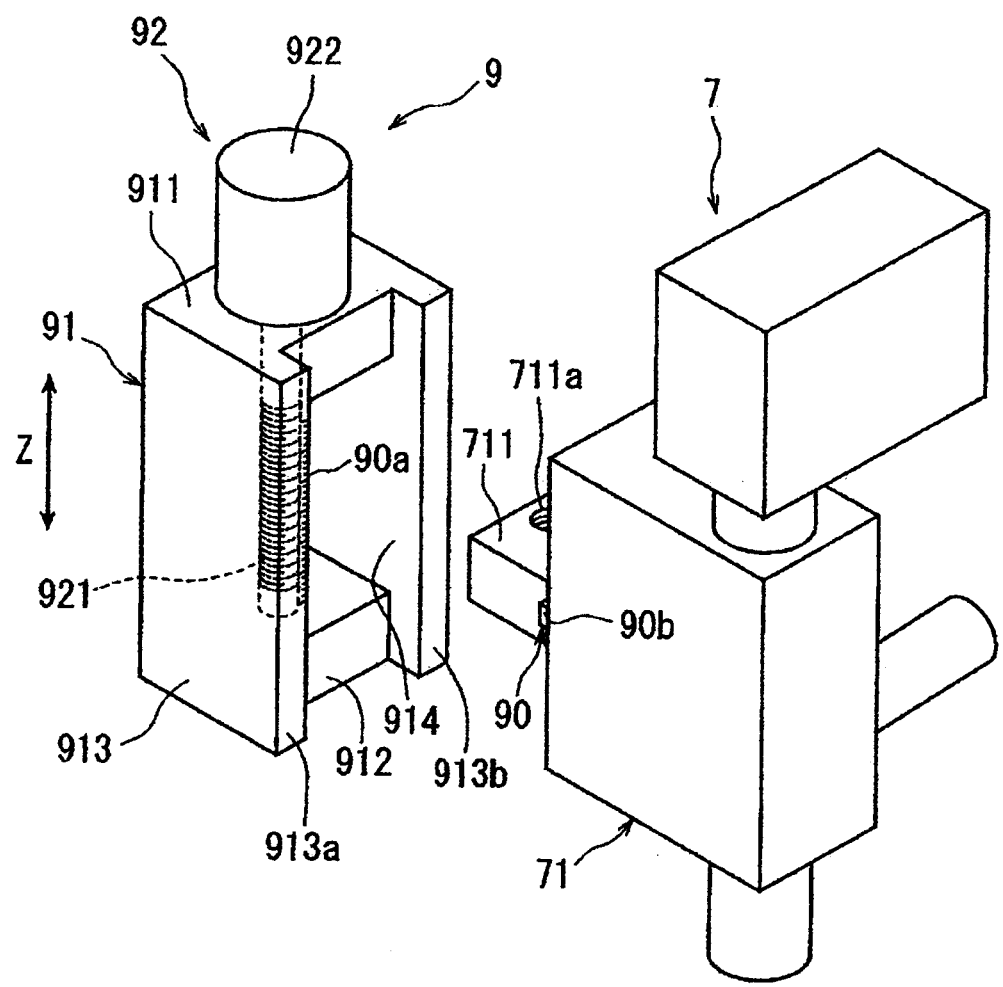
FIG. 4 is a perspective view showing, in an exploded state, the unevenness detecting device provided to the laser processing machine shown in FIG. 1 and Z-axis moving means supporting the unevenness detecting device movably in a Z-axis direction.

The Z-axis moving means 9 that movably supports the unevenness detecting device 7 in the Z-axis direction will next be described with reference to FIG. 4. The Z-axis moving means 9 includes: a supporting case 91 movably supporting the device housing 71 of the unevenness detecting device 7 in the Z-axis direction indicated by an arrow Z (direction perpendicular to the holding surface of the chuck table 36); and actuating means 92 for moving the device housing 71 supported by the supporting case 91 in the Z-axis direction indicated by the arrow Z. The supporting case 91 is formed by an upper wall 911, a bottom wall 912, both side walls 913 and 914, and a rear wall (not shown). Both side walls 913 and 914 project to the front to form guide rails 913a and 913b. The actuating means 92 includes: a male screw rod 921 disposed between and in parallel with both side walls 913 and 914 of the supporting case 91 and rotatably supported by the upper wall 911 and the bottom wall 912; and a driving source such as a pulse motor 922 or the like disposed on the upper wall 911 and transmissively coupled to the male screw rod 921. The male screw rod 921 of the thus formed actuating means 92 is screwed into a through female screw hole 711a formed in a female screw block 711 disposed on the rear wall of the device housing 71. Hence, the device housing 71 mounted with the female screw block 711 is moved in the Z-axis direction along the guide rails 913a and 913b by driving the male screw rod 921 for normal rotation and reverse rotation by the pulse motor 922.

The Z-axis moving means 9 in the present embodiment includes Z-axis direction position detecting means 90 for detecting the Z-axis direction position of the unevenness detecting device 7. The Z-axis direction position detecting means 90 includes: a linear scale 90a disposed on the guide rail 913a; and a read head 90b attached to the device housing 71 of the unevenness detecting device 7 and moved along the linear scale 90a together with the device housing 71. The read head 90b of the thus formed Z-axis direction position detecting means 90 sends a pulse signal of one pulse per μm in the embodiment shown in the figures to the control means to be described later.

Figure 5:
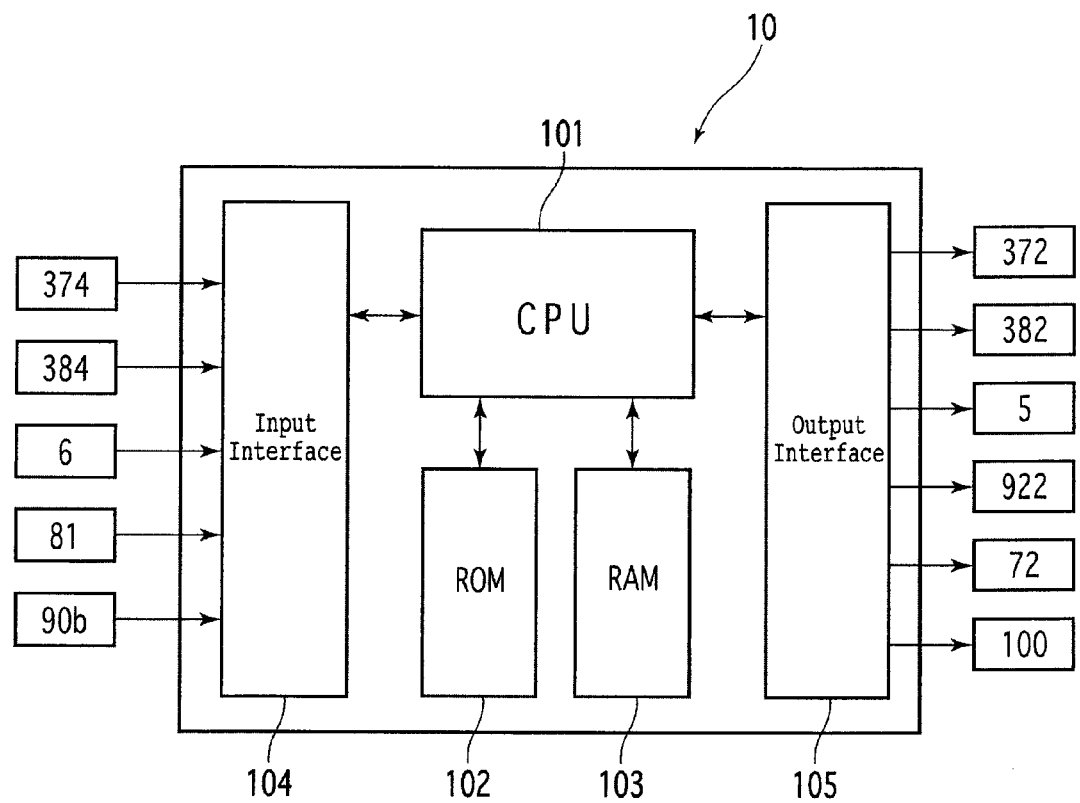
FIG. 5 is a block diagram showing control means of the unevenness detecting device.

The unevenness detecting device 7 in the present embodiment includes control means 10 shown in FIG. 5 which control means generates image information on the basis of an image signal output from the imaging element 81. Incidentally, the control means 10 controls not only constituent means of the unevenness detecting device 7 but also constituent means of the laser processing machine 1. The control means 10 is formed by a computer. The control means 10 includes: a central processing unit (CPU) 101 performing arithmetic processing according to a control program; a read only memory (ROM) 102 storing the control program and the like; a readable and writable random access memory (RAM) 103 storing operation results and the like; and an input interface 104 and an output interface 105. The input interface 104 of the control means 10 is supplied with detection signals from the X-axis direction position detecting means 374, the Y-axis direction position detecting means 384, the imaging means 6, the imaging element 81, the read head 90b of the Z-axis direction position detecting means 90, and the like. The output interface 105 of the control means 10 outputs control signals to the pulse motor 372 of the X-axis moving means 37, the pulse motor 382 of the Y-axis moving means 38, the laser beam irradiating means 5, the pulse motor 922 of the Z-axis moving means 9, the pulsed illuminating light source 72, and output means 100 such as display means, a printer, and the like. Incidentally, the random access memory (RAM) 103 has a storage area for storing images generated by the imaging element 81 and the like.

The laser processing machine 1 in the present embodiment is formed as described above. The action of the laser processing machine 1 will be described in the following.

Figure 6:
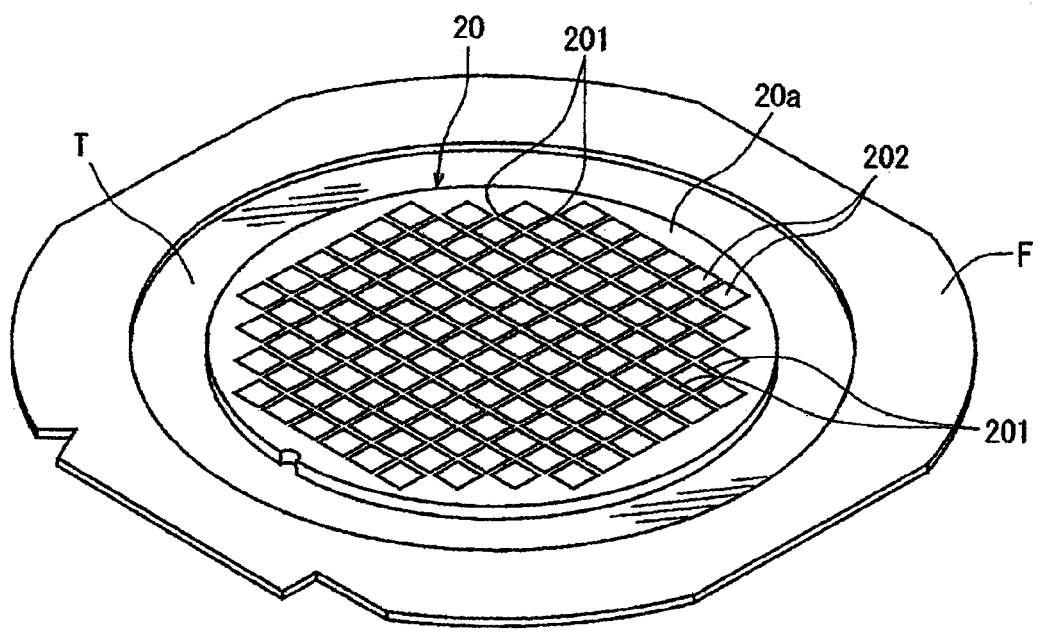
FIG. 6 is a perspective view of a state in which a semiconductor wafer as a workpiece is mounted on the top surface of a dicing tape fitted to an annular frame.

FIG. 6 is a perspective view showing a state in which a semiconductor wafer 20 as a workpiece to be processed by the above-described laser processing machine 1 is mounted on the top surface of a dicing tape T fitted to an annular frame F. The semiconductor wafer 20 shown in FIG. 6 is formed by a silicon wafer. A plurality of predetermined division lines 201 are formed in a lattice manner on a top surface 20a of the semiconductor wafer 20, and devices 202 such as ICs, LSIs, and the like are formed in a plurality of regions partitioned by the plurality of predetermined division lines 201.

Description will be made of an embodiment of laser processing for forming a laser-processed groove on the inside of the semiconductor wafer 20 along a predetermined division line 201 of the semiconductor wafer 20 by applying a laser beam along the predetermined division line 201 using the above-described laser processing machine 1.

First, the side of the dicing tape T to which the semiconductor wafer 20 is stuck is mounted on the chuck table 36 of the laser processing device 1 shown in FIG. 1 described above, and the semiconductor wafer 20 is sucked and held onto the chuck table 36 via the dicing tape T. Hence, the top surface 20a of the semiconductor wafer 20 sucked and held on the chuck table 36 via the dicing tape T faces upward. Incidentally, the annular frame F to which the dicing tape T is fitted is fixed by the clamp 362 disposed on the chuck table 36. The chuck table 36 thus sucking and holding the semiconductor wafer 20 is positioned directly under the imaging means 6 by the X-axis moving means 37.

After the chuck table 36 is positioned directly under the imaging means 6 as described above, the imaging means 6 and the control means 10 perform alignment operation in which a processing region to be laser-processed in the semiconductor wafer 20 is detected. Specifically, the imaging means 6 and the control means 10 perform image processing such as pattern matching or the like for alignment between a predetermined division line 201 formed in a predetermined direction on the semiconductor wafer 20 and the processing head 51 of the laser beam irradiating means 5, and thereby carry out alignment. In addition, alignment is similarly carried out for a predetermined division line 201 formed in a direction orthogonal to the predetermined direction on the semiconductor wafer 20.

Figure 7A:
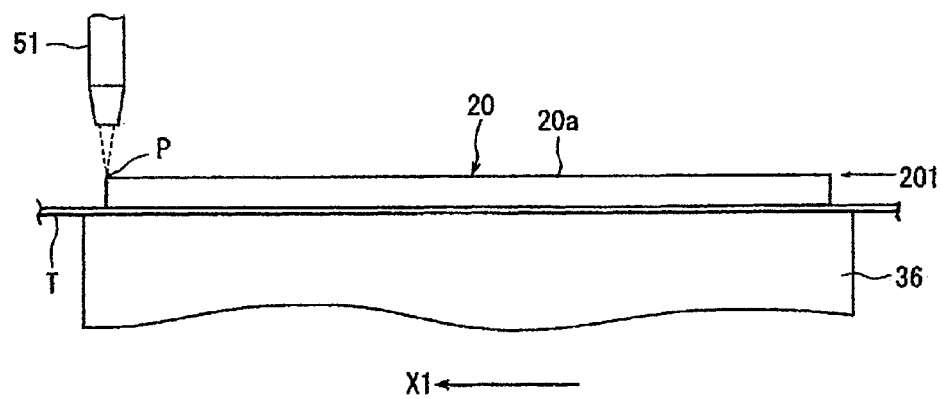
FIGS. 7A to 7C are diagrams of assistance in explaining a laser-processed groove forming process by the laser processing machine shown in FIG. 1.
Figure 7B:
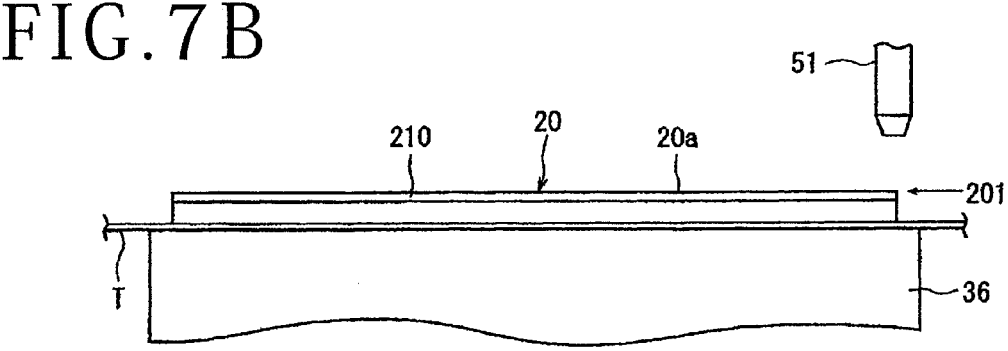
Figure 7C:
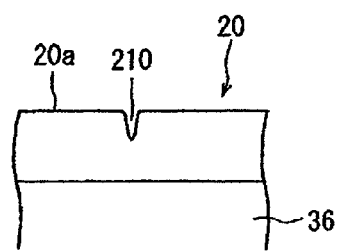

After the alignment is performed as described above, the control means 10 moves the chuck table 36 to position one end (left end in FIG. 7A) of a predetermined division line 201 directly under the processing head 51 of the laser beam irradiating means 5 as shown in FIG. 7A. Then, a focal point P of a pulsed laser beam applied from the processing head 51 is set in the vicinity of the top surface 20a (upper surface) of the semiconductor wafer 20. Next, the control means 10 moves the chuck table 36 at a predetermined processing feed speed in a direction indicated by an arrow X1 in FIG. 7A by operating the X-axis moving means 37 while applying the pulsed laser beam having a wavelength capable of being absorbed by the semiconductor wafer 20 from the processing head 51 of the laser beam irradiating means 5. Then, when another end (right end in FIG. 7B) of the predetermined division line 201 has reached a position directly under the processing head 51, the application of the pulsed laser beam by the laser beam irradiating means 5 is stopped, and the movement of the chuck table 36 is stopped. As a result, as shown in FIG. 7B and FIG. 7C, a laser-processed groove 210 is formed along the predetermined division line 201 on the semiconductor wafer 20 (laser-processed groove forming process).

The above-described laser-processed groove forming process is performed under the following processing conditions, for example.

Wavelength: 355 nm
Repetition frequency: 50 kHz
Average output: 5 W
Condensed spot diameter: 10 μm
Processing feed speed: 200 mm/second Next, a laser-processed groove checking process for checking the processed state of the laser-processed groove 210 formed by performing the above-described laser-processed groove forming process is performed. In the laser-processed groove checking process, the X-axis moving means 37 is operated to move the chuck table 36, on which the semiconductor wafer 20 resulting from the laser-processed groove forming process is held, to a position under the unevenness detecting device 7, and the laser-processed groove 210 formed in the semiconductor wafer 20 is positioned directly under the chromatic aberration lens 75. The Z-axis moving means 9 is next operated to lower the unevenness detecting device 7 from a standby position and position the unevenness detecting device 7 at a predetermined detection position.

Figure 8A:
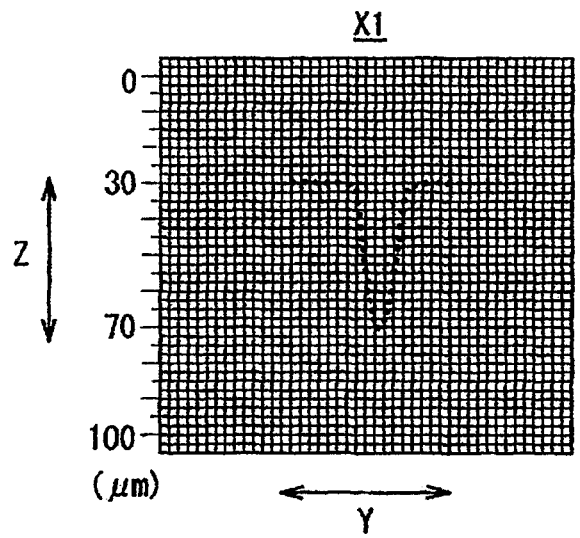
FIG. 8A to 8C are diagrams of assistance in explaining images of two-dimensional sectional shapes output by an imaging element of the unevenness detecting device.
Figure 8B:
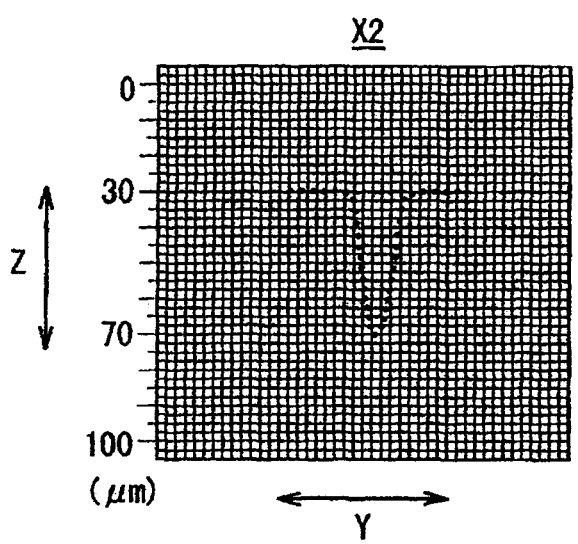
Figure 8C:
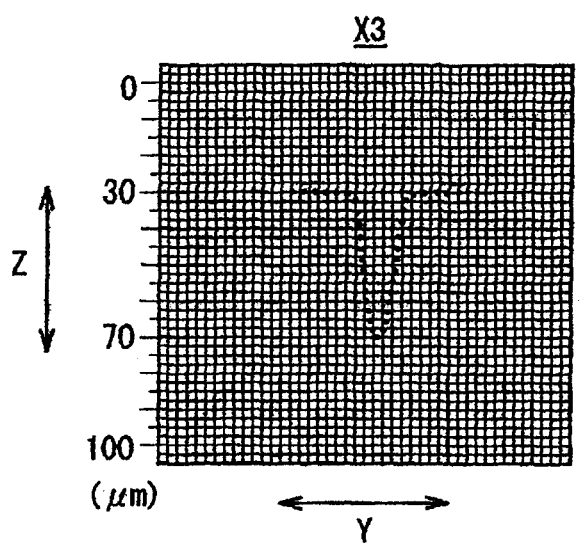

Next, the pulsed illuminating light source 72 forming the detection light irradiating means 70 of the unevenness detecting device 7 is operated to emit light having a predetermined wavelength range (for example 400 nm to 800 nm). The light emitted by the pulsed illuminating light source 72 is applied to the laser-processed groove 210 formed in the semiconductor wafer 20 via the first converging lens 73, the half-silvered mirror 74, and the chromatic aberration lens 75. The light thus applied to the laser-processed groove 210 formed in the semiconductor wafer 20 is reflected by the top surface of the semiconductor wafer 20 and the wall surfaces of the laser-processed groove 210, and the return light is guided to the diffraction grating 79 via the chromatic aberration lens 75, the half-silvered mirror 74, the first condensing lens 76, the slit 771 of the mask 77, and the second converging lens 78. The return light guided to the diffraction grating 79 is subjected to light separation so as to correspond to the wavelengths of the return light, and then reaches the imaging element 81 via the second condensing lens 80. The imaging element 81 generates a two-dimensional sectional shape in the Y-axis direction (width direction of the laser-processed groove 210) and the Z-axis direction (depth direction of the laser-processed groove 210) as shown in FIG. 8 on the basis of the light intensity of the light that has been subjected to the light separation so as to correspond to the wavelengths. The imaging element 81 outputs the two-dimensional sectional shape to the control means 10.

When this operation is performed, the control means 10 operates the X-axis moving means 37, and obtains two-dimensional sectional shapes in the Y-axis direction (width direction of the laser-processed groove 210) and the Z-axis direction (depth direction of the laser-processed groove 210) at respective positions in the X-axis direction (X1, X2, X3, . . . ) as shown in FIG. 8. The control means 10 stores the two-dimensional sectional shapes in the random access memory (RAM) 103, and outputs the two-dimensional sectional shapes to the output means 100 to make the display means such as a monitor or the like display the two-dimensional sectional shapes or make the printer print out the two-dimensional sectional shapes. The processed state of the laser-processed groove 210 can be verified when the display means such as the monitor or the like as the output means 100 is thus made to display the two-dimensional sectional shapes of the laser-processed groove 210 or the printer as the output means 100 is thus made to print out the two-dimensional sectional shapes of the laser-processed groove 210.

Figure 9:
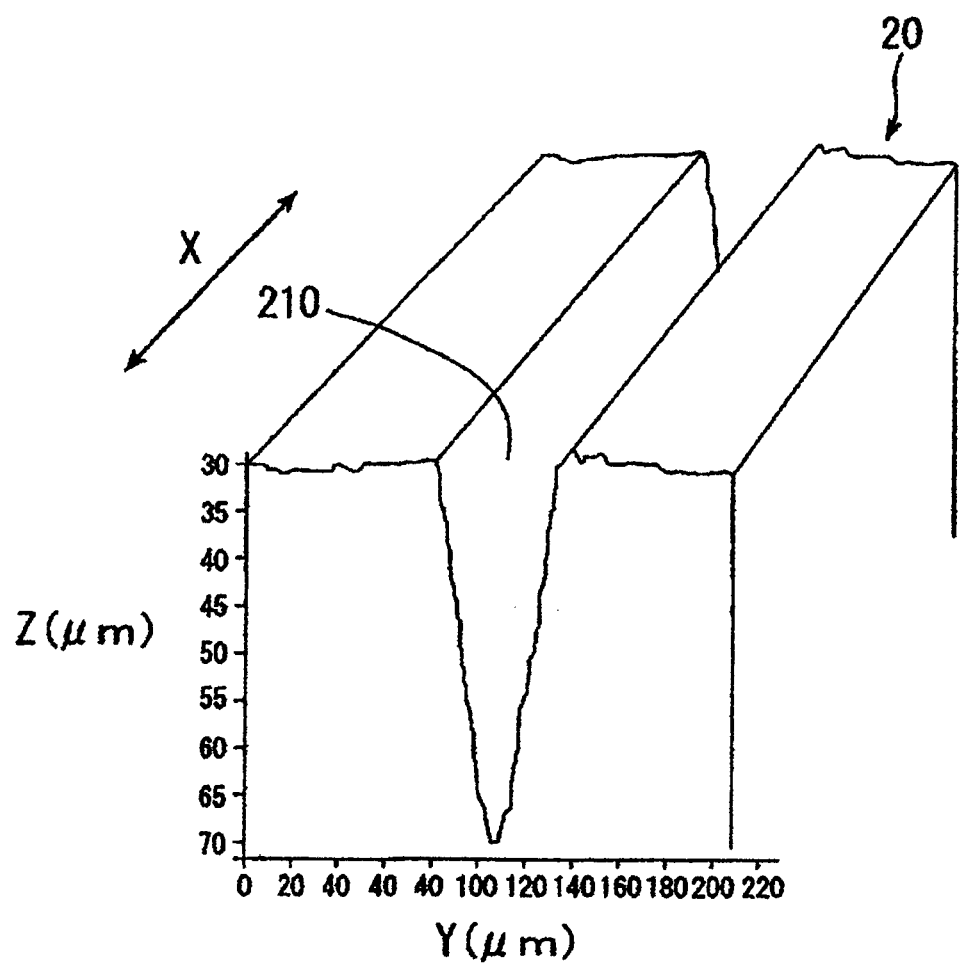
FIG. 9 is a diagram of assistance in explaining an image of a three-dimensional shape of a laser-processed groove which image is generated on the basis of the two-dimensional sectional shapes in a Y-axis direction which two-dimensional sectional shapes are shown in FIG. 8.

Next, the control means 10 creates a three-dimensional shape as shown in FIG. 9 by arranging, in the X-axis direction, the two-dimensional sectional shapes in the Y-axis direction (width direction of the laser-processed groove 210) and the Z-axis direction (depth direction of the laser-processed groove 210) at the respective positions in the X-axis direction (X1, X2, X3, . . . ), the two-dimensional sectional shapes being stored in the random access memory (RAM) 103. The control means 10 stores the three-dimensional shape in the random access memory (RAM) 103, and outputs the three-dimensional shape to the output means 100 to make the display means such as the monitor or the like display the three-dimensional shape or make the printer print out the three-dimensional shape. When the three-dimensional shape of the laser-processed groove 210 is thus obtained, the processed state can be verified minutely. It is therefore possible to set appropriate processing conditions by adjusting the processing conditions.

The present invention has been described above on the basis of the embodiments shown in the figures. However, the present invention is not limited only to the foregoing embodiments, but are susceptible of various modifications within the scope of the spirit of the present invention. For example, while an example in which the present invention is applied to a laser processing machine has been illustrated in the foregoing embodiments, the present invention can be applied to a cutting machine to verify the depth and sectional shape of cut grooves, and can be applied to a grinding machine to verify the state of unevenness of traces of grinding.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. An unevenness detecting device detecting unevenness of a workpiece retained by workpiece holding means, the unevenness detecting device comprising:
    a pulsed illuminating light source emitting light having a predetermined wavelength range;
    a first converging lens converging the light emitted by the pulsed illuminating light source;
    a half-silvered mirror branching the light converged by the first converging lens;
    a chromatic aberration lens condensing the light branched by the half-silvered mirror and irradiating the workpiece retained by the workpiece holding means with the condensed light;
    a first condensing lens condensing return light reflected by the workpiece retained by the workpiece holding means and passed through the chromatic aberration lens and the half-silvered mirror;
    a mask disposed at a position of a focal point of the first condensing lens, the mask passing only the condensed return light;
    a second converging lens converging the return light passed through the mask;
    a diffraction grating performing light separation so as to correspond to wavelengths of the return light converged by the second converging lens;
    a second condensing lens condensing the return light resulting from the light separation by the diffraction grating;

an imaging element disposed at a position of a focal point of the second condensing lens;

control means including a memory storing an image generated by the imaging element; and output means displaying the image stored in the memory of the control means;

wherein when a width direction of a detection region in which to detect the unevenness of the workpiece retained by the workpiece holding means is a Y-axis direction, and a longitudinal direction of the detection region is an X-axis direction, the mask has a slit extending in the Y-axis direction, and the imaging element generates a two-dimensional sectional shape in the Y-axis direction on a basis of the return light passed through the slit formed in the mask.

2. The unevenness detecting device according to claim 1, wherein the control means stores two-dimensional sectional shapes in the Y-axis direction in the memory while moving the workpiece holding means in the X-axis direction, and generates a three-dimensional shape by arranging, in the X-axis direction, the two-dimensional sectional shapes in the Y-axis direction, the two-dimensional sectional shapes in the Y-axis direction being stored in the memory.

3. The unevenness detecting device according to claim 1, wherein the unevenness detecting device is provided to a processing machine including processing means processing the workpiece retained by the workpiece holding means, and processing feed means performing processing feed of the workpiece holding means and the processing means relative to each other in the X-axis direction.

\* \* \* \* \*